US009656812B2

(12) United States Patent
Voth et al.

(10) Patent No.: US 9,656,812 B2
(45) Date of Patent: May 23, 2017

(54) DEVICE FOR STERILIZING PLASTIC PARISONS

(71) Applicant: Krones AG, Neutraubling (DE)

(72) Inventors: Klaus Voth, Obertraubling (DE); Roland Laumer, Regensburg (DE); Gerald Hüttner, Vilseck (DE); Jürgen Söllner, Beratzhausen (DE); Michael Loy, Regensburg (DE)

(73) Assignee: KRONES AG, BÖHMERWALDSTRASSE 5, Neutraubling (DE)

( * ) Notice: Subject to any disclaimer, the term of this patent is extended or adjusted under 35 U.S.C. 154(b) by 0 days.

(21) Appl. No.: 14/099,958

(22) Filed: Dec. 8, 2013

(65) Prior Publication Data
US 2014/0158500 A1    Jun. 12, 2014

(30) Foreign Application Priority Data

Dec. 12, 2012    (DE) .................. 10 2012 112 158

(51) Int. Cl.
*B65B 55/08*    (2006.01)
*A61L 2/08*    (2006.01)
(Continued)

(52) U.S. Cl.
CPC ............... *B65G 35/06* (2013.01); *A61L 2/08* (2013.01); *A61L 2/087* (2013.01);
(Continued)

(58) Field of Classification Search
CPC ..... B29C 49/4252; A61L 2/087; B65G 35/06; B65B 55/08
See application file for complete search history.

(56) References Cited

U.S. PATENT DOCUMENTS 5,049,750 A * 9/1991 Hoshino ................. B29C 49/78
250/223 B
5,598,859 A * 2/1997 Kronseder ............. B08B 9/426
134/152
(Continued)

FOREIGN PATENT DOCUMENTS

DE    G8122185.1 U1    12/1981
EP    2 213 578 A1    8/2010
(Continued)

OTHER PUBLICATIONS

China Patent Office Action dated Nov. 25, 2015.
(Continued)

*Primary Examiner* — Thomas Randazzo
(74) *Attorney, Agent, or Firm* — Oppedahl Patent Law Firm LLC

(57) ABSTRACT

The invention relates to a device (100) for sterilizing plastic parisons (1), with a sterilization chamber (3) and a transport device (2) disposed at least partially inside the sterilization chamber (3) for moving the plastic parisons (1) within the sterilization chamber (3), wherein the transport device (2) has at least one gripping system (4) for engaging round and supporting the plastic parisons (1) by means of a gripping clamp (41), wherein the gripping system (4) has a displacement means (5) for displacement during sterilization within the sterilization chamber of contact surfaces (1A) of the plastic parisons (1) which are shielded by the gripping system (4) from a sterilizing medium and/or sterilizing radiation.

9 Claims, 3 Drawing Sheets

(51) Int. Cl.
*B65G 35/06* (2006.01)
*B65B 43/46* (2006.01)
*B65B 55/04* (2006.01)
*B29C 49/42* (2006.01)
*B67C 3/22* (2006.01)

(52) U.S. Cl.
CPC .......... *B29C 49/4252* (2013.01); *B65B 43/46* (2013.01); *B65B 55/04* (2013.01); *B65B 55/08* (2013.01); *A61L 2202/23* (2013.01); *B29C 49/4205* (2013.01); *B67C 2003/228* (2013.01)

(56) References Cited

U.S. PATENT DOCUMENTS

| | | | |
|---|---|---|---|
| 6,582,217 B1 | 6/2003 | Achhammer | |
| 8,293,173 B2 * | 10/2012 | Bufano | A61L 2/087 250/492.1 |
| 2006/0192140 A1 * | 8/2006 | Nablo | A61L 2/08 250/492.1 |
| 2010/0054987 A1 * | 3/2010 | Krueger | A61L 2/082 422/3 |
| 2010/0061831 A1 * | 3/2010 | Nishino | A61L 2/087 414/225.01 |
| 2010/0123090 A1 * | 5/2010 | Nishino | A61L 2/087 250/491.1 |
| 2010/0202918 A1 * | 8/2010 | Kobayashi | A61L 2/087 422/22 |
| 2010/0270477 A1 * | 10/2010 | Nishino | A61L 2/087 250/455.11 |
| 2011/0012032 A1 * | 1/2011 | Bufano | A61L 2/087 250/492.3 |
| 2013/0154164 A1 | 6/2013 | Laumer | |
| 2013/0272920 A1 | 10/2013 | Knott | |

FOREIGN PATENT DOCUMENTS

| | | |
|---|---|---|
| EP | 2 371 397 A1 | 10/2011 |
| EP | 2 394 950 A1 | 12/2011 |
| EP | 2 594 495 A1 | 5/2013 |
| EP | 2 604 410 A1 | 6/2013 |
| EP | 2 650 022 A1 | 10/2013 |
| WO | 9964220 A1 | 12/1999 |

OTHER PUBLICATIONS

European Search Report in application No. EP 13 19 6192, dated Jan. 28, 2014.
Machine Translation of DE Patent No. G8122185.1, patent originally published Dec. 3, 1981. (4 pages).

* cited by examiner

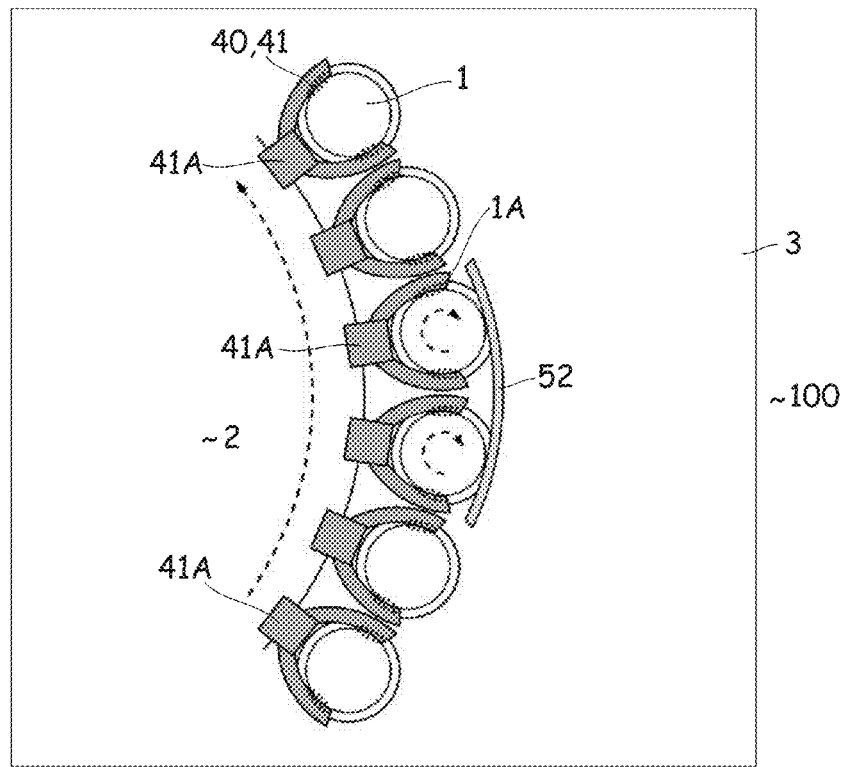
Fig. 1C
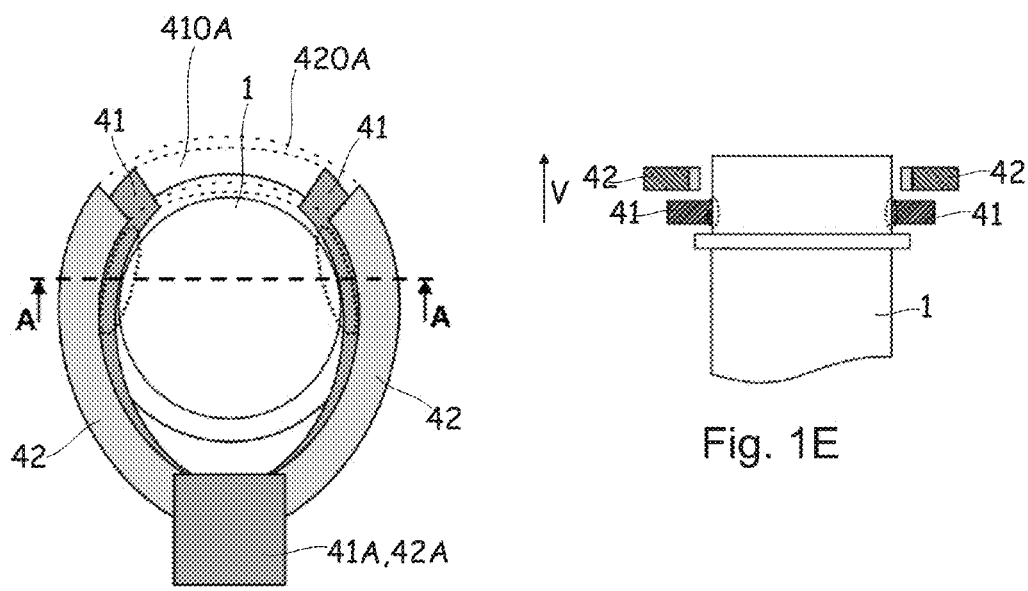
Fig. 1D
Fig. 1E

DEVICE FOR STERILIZING PLASTIC PARISONS

BACKGROUND

The invention relates to a device for sterilizing containers, in particular plastic containers and in particular plastic parisons, and also a method for sterilizing containers, in particular plastic containers and in particular plastic parisons. It is pointed out that the invention is described below with reference to plastic parisons described is and also only plastic parisons will be discussed. However, the invention is also applicable correspondingly to the sterilization of containers and in particular of plastic containers. However, the invention is particularly suitable for plastic parisons, since these have a relatively low weight and can also be sterilized relatively simply with regard to their size.

The device for sterilizing plastic parisons comprises a sterilization chamber and a transport device disposed at least partially inside the sterilization chamber for moving the plastic parisons inside the sterilization chamber, wherein the transport device has at least one gripping system for engaging round and supporting the plastic parisons by means of a gripping clamp. Engaging round is understood to mean at least partially engaging round, and thus within the scope of the invention it is not absolutely necessary for the plastic parison to be completely engaged around in its circumferential direction.

Generic devices for sterilizing plastic parisons are already known from the prior art. In this case the plastic parisons are guided through a sterilization chamber by means of the transport device and during this transport they are for example sterilized by means of a sterilizing medium. In order to be able to appreciably improve the shelf life of sensitive products to be filled for example into PET bottles, before the filling process the number of germs in the containers must be significantly reduced. For this purpose various wet and dry aseptic methods are known in the field of filling technology, but because of the sometimes large bottle volumes these methods give rise to a high consumption of the sterilizing medium used (for example peracetic acid, $H_2O_2$, . . . ). Therefore further machine designs reduce the number of germs even before the plastic parisons are blow moulded. In this case the plastic parison runs through a treatment region, that is to say a sterilization chamber, in which the disinfection is achieved by gaseous or liquid sterilization media or by irradiation (UV radiation, electron beams).

However, devices which are known from the prior art for sterilizing the plastic parisons have the inherent disadvantage that they cannot meet the particularly high demands for disinfection performance (e.g. in the case of weakly acidic products to be filled). In general during the container handling it should be ensured that every region of the container comes into contact for a specific time with the sterilizing means, i.e. a sterilizing medium or the radiation. Such sterilization which is as comprehensive as possible and covers the greatest possible surface area is desirable in particular in the case of subsequent filling with weakly acidic products. In this case a problem is posed by the gripping system in that at the points where a gripping clamp is positively or non-positively engaged on the plastic parison, that is to say on contact surfaces between the gripping clamp and the plastic parison, sterilization by the sterilizing means is not possible or is only possible to an insufficient extent. In other words, such contact surfaces on an external surface of the plastic parison are concealed by the gripping clamp. As a result, disinfection of these contact surfaces on this external surface is not ensured or is at least difficult, which is problematic in particular in the mouth region close to the product to be filled.

Therefore an object to be achieved is to provide a cost-effective device for sterilizing plastic parisons in which an external surface of plastic parisons can be completely sterilized in the simplest manner possible.

SUMMARY OF THE INVENTION

This is achieved according to the invention by a device for sterilizing plastic parisons and a method sterilizing plastic parisons. Advantageous embodiments and modifications are the subject matter of the subordinate claims.

In order to propose a device for sterilizing plastic parisons, wherein an external surface of the plastic parisons can be completely sterilized in a particularly simple and cost-effective manner, the present invention makes use inter alia of the idea that the gripping system has a displacement means for displacement, during sterilization within the sterilization chamber, of contact surfaces on an external surface of the plastic parisons which are shielded by the gripping system from a sterilizing medium and/or a sterilizing radiation. If a plastic parison is to be guided by means of the gripping clamps over the transport device through the sterilization chamber it is conceivable that, after a predeterminable partial sterilization time, during gripping by the gripping system, for example by means of a non-positively engaging contact between the displacement means and the plastic parison, the displacement means twists and/or shifts the plastic parison within the gripping system. Contact surfaces on the external surface of the plastic parison which at the start of the sterilization were still concealed by the gripping system from sterilization, are now free after for example the twisting of the plastic parison by the displacement means and thus for the remaining sterilization time these surfaces can also be completely sterilized. Therefore such a displacement means enables the most comprehensive and complete sterilization possible over the entire external surface of the plastic parison, without the need to interrupt the sterilization process or to displace the plastic parison by means of further expensive engaging or shifting mechanisms.

According to at least one embodiment the device for sterilizing plastic parisons comprises a sterilization chamber and a transport device disposed at least partially inside the sterilization chamber for moving the plastic parisons inside the sterilization chamber, wherein the transport device has at least one gripping system for engaging round and supporting the plastic parisons by means of a gripping clamp. The gripping system has a displacement means for displacement, during sterilization within the sterilization chamber, of contact surfaces on an external surface of the plastic parisons which are shielded by the gripping system from a sterilizing medium.

The device preferably has at least one application device by which a free-flowing sterilizing medium (for example hydrogen peroxide and/or peracetic acid) is applied to the plastic parisons and/or a radiation device by which radiation, in particular electromagnetic radiation, or charge carriers, in particular electrons (although protons or alpha particles for instance would also be conceivable) are applied to the plastic parisons. In this case an application device and/or a radiation device is advantageously disposed in a stationary manner.

According to at least one embodiment the displacement means is formed with at least one drive roller which is disposed rotatably within the gripping clamp and is in non-positive engagement with the plastic parison, and wherein by means of a rotation of the drive roller about its axis of rotation, relative to gripping arms of the gripping clamp, in one direction of rotation, a rotation of the plastic parison around its axis of rotation, relative to the gripping arms, can be effected, wherein the two directions of rotation are in each case opposed. This means that during the engagement and support by the gripping clamp the plastic parison is turned inside the gripping clamp by means of the drive roller. For example, at the start of a sterilization process within the sterilization chamber, points on the external surface of the plastic parison which are concealed from the sterilizing medium by the gripping arms are therefore exposed for the sterilizing medium by the rotation. In this way it is ensured particularly simply that all external surface regions of the plastic parison come into contact for a sufficient time with the sterilizing means, for example a sterilizing medium or radiation.

According to at least one embodiment the drive roller is rotatable by means of a pneumatic, mechanical, electrical or hydraulic drive. For this purpose the drive can be surrounded by the gripping system or the drive can be disposed separately from the gripping system in a mechanically fixed manner on the transport device and/or within the sterilization chamber.

According to at least one embodiment the displacement means is formed with at least one friction rail, wherein the plastic parison is guidable along this friction rail within the sterilization chamber, wherein by means of a non-positive engagement between the plastic parison and the friction rail the plastic parison is rotatable about its axis of rotation within the gripping clamp, that is to say during the engagement and support. The plastic parisons are therefore guided past on the friction rail, which leads directly to a rotation of the plastic parisons within the gripping arms of the gripping clamp.

The longer the friction rail is, the longer the plastic parisons are in non-positive engagement with this friction rail and are rotated corresponding to the length of the friction rail and preferably over the total extent of the length of the friction rail. In other words, the length of the friction rail determines a twisting angle of the plastic parisons from the starting position. Setting of the twisting angle is made possible particularly simply by means of such a friction rail. It is conceivable that for setting the twisting angle various friction rails are retained in the device and the length of the friction rail is chosen according to the requirements and construction of the gripping arms which determine a surface area dimension of the contact surfaces between the gripping arms and the plastic parisons. Alternatively the length of a friction rail can be changed, for example telescopically.

According to at least one embodiment the displacement means is formed with at least one further gripping clamp, wherein two gripping clamps are disposed in the vertical direction at least partially overlapping and spaced apart from one another in this direction. The "vertical direction" is a direction perpendicular to a transport plane of the transport device. In this case during the sterilization at least one gripping clamp is operatable in an open position and a gripping clamp which is different therefrom is operatable in a closed position, wherein after a predeterminable partial sterilization time the respective other gripping clamp is operatable in an open position or in a closed position.

In other words, during the sterilization inside the sterilization chamber at least one gripping clamp is closed and engages non-positively with the plastic parison. Therefore the plastic parison is always firmly engaged around and retained by at least one gripping clamp during the sterilization. If the displacement means is formed for example by two gripping clamps, the respective other gripping clamp is in the open position, i.e. this gripping clamp is preferably not in contact, in particular not in non-positively engaging contact, with the plastic parison.

After the expiry of the predeterminable partial sterilization time, the further gripping clamp which was hitherto operated in the open position now engages the plastic parison by means of its gripping arms. Immediately after the engagement of the further gripping clamp, the gripping clamp which up to this time is still closed now opens and is operated in the open position. In other words, after expiry of the partial sterilization time, for the remaining sterilization time the further gripping clamp is still in the closed position and engages non-positively around the plastic parison, whilst the gripping clamp is consequently no longer in direct contact, in particular not in non-positively engaging contact, with the plastic parison.

Respective contact surfaces on the external surface of the plastic parison, between the plastic parison and the gripping arms of the gripping clamps, are therefore displaced after the respective expiration the partial sterilization time has elapsed. Therefore contact surfaces which were previously defined up to the expiry of the partial sterilization time are freely accessible to the sterilizing means after the expiry of the partial sterilization time, whilst already sterilized contact surfaces, which are shifted by the gripping by the further gripping clamp by means of its gripping arms, are now shielded from the sterilizing means.

According to at least one embodiment, clamp joints of the gripping clamps are disposed above one another in the vertical direction, wherein respective clamp openings of the two gripping clamps overlap at least partially in the vertical direction. In this case the clamp joints of the gripping clamp are the joints in which the gripping arms associated with the respective gripping clamps are rotatable and jointly supported. Clamp openings are the regions of the gripping clamp which are opposite the clamp joints and which in the closed position of the gripping clamp is free of the gripping arms. Therefore the clamp openings form a gap between the gripping clamps.

Preferably both gripping clamps are jointly fastened mechanically to the transport device. In other words, in this case the gripping system comprises at least two pairs of gripping arms of two gripping clamps, wherein both gripping clamp are firmly mounted on the transport device. Therefore engagement round, i.e. displacement of the contact surfaces, which is described in this embodiment can be achieved particularly simply by one and the same transport device.

According to at least one embodiment the gripping clamps are disposed on different clamp joints which lie opposite one another in the horizontal direction, wherein the clamp joint of the further gripping clamp is fastened on a further transport device which is disposed at least partially within the sterilization chamber. The "horizontal direction" is a direction parallel to the transport plane of the transport device. Both transport devices are preferably disposed completely inside the sterilization chamber. Engagement round, i.e. displacement of the contact surfaces between the gripping clamps and the plastic parison therefore takes place between these two gripping clamps which are disposed separately and apart from one another.

In this case the gripping clamp, which is preferably connected to the transport system and preferably mechanically fastened thereon, transfers the plastic parison to the further gripping clamp, which is preferably connected to the transport system and preferably mechanically fastened thereon. In this respect after expiry of the partial sterilization time the plastic parison held by the gripping clamp is transferred to the further gripping clamp. After the non-positively engaging gripping by the further gripping clamp around the plastic parison the gripping clamp is then released, so that during the transfer for a predeterminable time period, which is preferably particularly short, both gripping clamps are operated in the closed position operated and therefore engage non-positively around the plastic parison during a transfer time thus defined.

However, the sterilization process is also advantageously continued during this engagement.

Furthermore, a method is provided for sterilizing containers and in particular plastic parisons. By means of the method described here a plastic parison can be sterilized, as has been described in connection with one or more of the embodiments set out above. In other words, the features listed for the device described here are also disclosed for the method described here, and vice versa.

In the method described here the plastic parisons are moved by means of a transport device disposed at least partially inside the sterilization chamber, wherein the transport device has at least one gripping system for engaging round and supporting the plastic parisons by means of a gripping clamp.

During a sterilization inside the sterilization chamber, after expiry of a predeterminable partial sterilization time, contact surfaces of the plastic parisons which are shielded from a sterilizing medium and/or sterilizing radiation are displaced by the gripping system by means of a displacement means. As already described in the introduction, such a displacement of the contact surfaces which are formed between gripping arms of the gripping clamp and the plastic parison enables the most complete sterilization possible of the entire surface of the plastic parison. This displacement can take place for example by means of a rotation of the plastic parison within the gripping clamp or by means of the plastic parison being engaged between the gripping clamp and at least one further gripping clamp, so that the respective contact surfaces of the plastic parisons are likewise displaced.

This displacement can also take place by shifting of the plastic parison in its longitudinal direction relative to the gripping element.

The device described here as well as the method described here are explained in greater detail below with reference to embodiments and the associated drawings.

DESCRIPTION OF THE DRAWING

FIGS. 1A to 1G show, in various schematic perspective views, embodiments of a device described here and also method steps for sterilizing plastic parisons.

In the embodiments and in the Figures the same or equivalent components are in each case provided with the same reference signs. The illustrated elements should be regarded as drawn to scale, on the contrary, individual elements may be shown as excessively large to aid understanding.

DETAILED DESCRIPTION

Figure 1A:
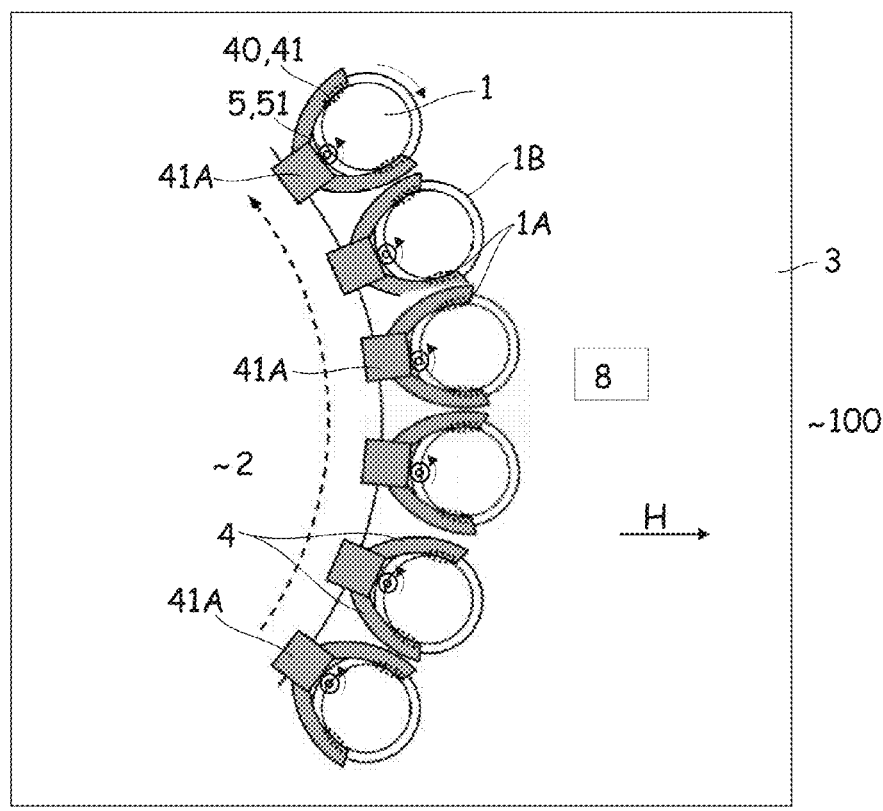

FIG. 1A shows a schematic plan view of a device 100 described here for sterilizing plastic parisons 1. The device 100 has a sterilization chamber 3 and a transport device 2 which is disposed (in particular rotatably) completely inside the sterilization chamber 3 for moving the plastic parisons 1 within the sterilization chamber 3. Each of the plastic parisons 1 is clamped around by gripping arms 40 of a respective gripping clamp 41. In this case clamp joints 41A of the gripping clamps 41 are firmly fixed mechanically along an arcuate path on the transport device 2. Furthermore in the embodiment of FIG. 1A it can be seen that the gripping system has a displacement means 5 for displacement, during sterilization within the sterilization chamber 3, of contact surfaces 1A on an external surface 1B of the plastic parisons 1 which are shielded by the gripping system 4 from a sterilizing medium.

In this case the displacement means 5 are constructed in each case in the form of a drive roller 51 which is disposed rotatable within each gripping clamp 41 and is in non-positive engagement with the plastic parison 1. In this case the drive roller 51 can be set in rotation for example by means of a pneumatic, mechanical, electrical or hydraulic drive. By means of a rotation of the drive roller 51 about its axis of rotation, relative to the gripping arms 40 of the gripping clamp 41 in one direction of rotation, a rotation of the plastic parison 1 about its axis of rotation, relative to the gripping arms 40 in the opposite direction is produced.

As can be seen from FIG. 1A, the drive roller 51 rotates in the direction towards the right, whilst the plastic parison 1 moves in the direction towards the left. In this case contact surfaces 1A, which are formed relative to the external surface 1B of the plastic parison 1 between the plastic parison 1 and the gripping arms 40 of the gripping clamps 41 on the external surface 1B, and which are concealed from a sterilizing means, are displaced on the outside surface 1B of the plastic parison 1. In this respect during the rotation the contact surfaces 1A are continuously shifted on the external surface 1B of the plastic parison 1, so that all regions of the external surface 1B of the plastic parison 1 are sterilized.

The reference sign 8 identifies schematically a radiation device which applies electrons to the plastic parisons for the purpose of sterilizing them. This application of electrons or generally charge carriers is referred to in the context of the present application as irradiation. Accordingly a charge carrier emitter is also regarded as a radiation device. In this case the said clean room which surrounds the plastic parisons during their sterilization can be enclosed in a stationary housing. However it would also be possible for the clean room to surround the transport path of the plastic parisons in the manner of an annular channel. The clean room can also be enclosed by at least one stationary wall and a wall which is movable relative to this stationary wall, wherein a sealing means, for instance like a so-called water lock, is preferably disposed between this stationary wall and the movable wall.

Figure 1B:
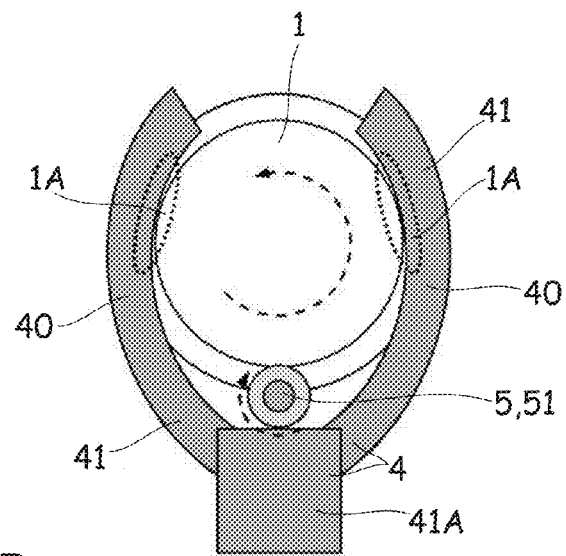

In FIG. 1B the gripping system 4 shown in FIG. 1A and the drive roller 51 are again shown in detail.

FIG. 1C shows a schematic plan view of a further embodiment of the device 100 described here, wherein instead of the drive roller 51 a friction rail 52 is implemented for rotation of the plastic parisons 1 inside the gripping clamps 41 during the engagement and support of the plastic parisons 1 by the gripping clamps 41. It can be seen that the friction rail 52 is disposed in the horizontal direction H opposite the respective clamp joints 41A. If the plastic parisons 1 are now guided along through the transport device 2 on the friction rail 52, that is to say past an external surface of the friction rail 52 facing the transport device 2, the plastic parisons 1 are set in rotation during the griping within the gripping clamps 41. A twisting angle of the plastic parisons 1 is therefore fixed directly by a length of the friction rail 52. By means of such a friction rail 52 it is therefore possible in a particularly simply manner to effect a displacement of the contact surfaces 1A.

FIGS. 1D and 1E show a schematic plan view and side view of a further embodiment of a device 100 described here, in which in contrast to the aforementioned embodiments the displacement means 5 has a further gripping clamp 42. Both gripping clamps 41, 42 are disposed so that they are partially overlapping in the vertical direction V (see FIG. 1E) and are spaced apart relative to one another in this vertical direction V. During sterilization at least one of the two gripping clamps 41, 42 is operated in a closed position. This means that in this closed position one of the two gripping clamps engages round and supports the respective plastic parison 1. Up to the expiry of a predeterminable partial sterilization time the gripping clamp 41 is for example in this closed position, whereas up to this time the further gripping clamp 42 is still operated in the open position.

At the expiry of the partial sterilization time engagement takes place. During this transfer time period both gripping clamps 41, 42 are in the closed position. After expiry of the transfer time period only the further gripping clamp 42 remains in the closed position and the gripping clamp 41 is now moved into the open position. In other words the plastic parison 1 is transferred from the gripping clamp 41 to the further gripping clamp 42, wherein during the transfer within the sterilization chamber 3 the plastic parison 1 always held by one of the two gripping clamps 41, 42. Furthermore it can be seen that both the clamp joint 41A of the gripping clamp 41 and also a clamp joint 42A of the further gripping clamp 42 are disposed above one another in the vertical direction V and respective clamp openings 410A, 420A of the two gripping clamp 41, 42 overlap at least partially in the vertical direction V. In this arrangement both gripping clamps 41, 42 are mechanically fastened on the same transport device 2.

Figure 1F:
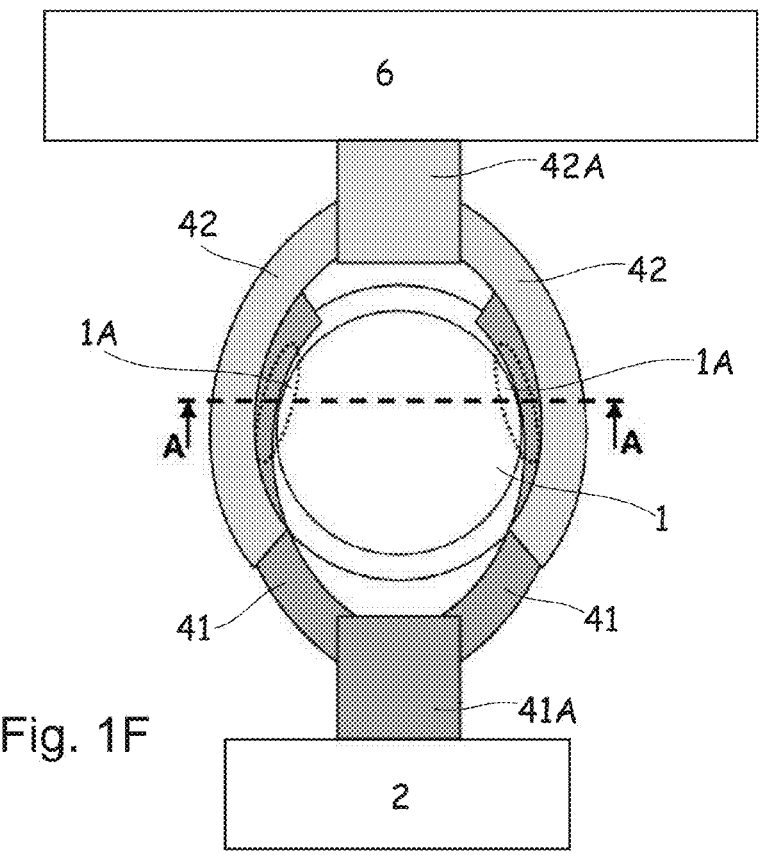
Figure 1G:
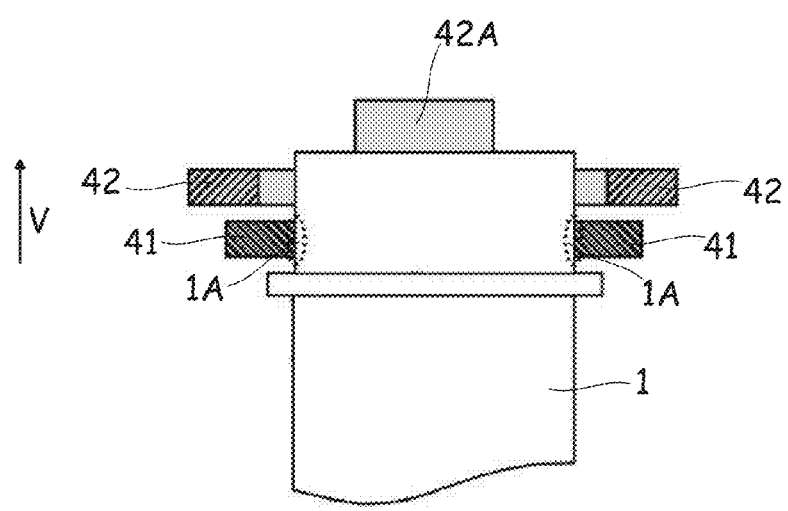

FIGS. 1F and 1G show a schematic plan view and side view of a further embodiment of a device 100 which is described here. In contrast to the device 100 shown in FIGS. 1D and 1E, the device 100 of FIGS. 1F and 1G exhibits the difference that the further gripping clamp 42 is mounted a further transport device 6 and is mechanically secured thereto. The transport devices 2 and 6 are synchronised with one another, in particular electrically or mechanically synchronised. In this respect the clamp joints 41A and the clamp joints 42A are in each opposed. Therefore by means of the device described in this embodiment different transport devices can be combined with one another in order to displace the contact surfaces 1A of the plastic parisons 1 during the sterilization.

The invention is not limited by the description with reference to the embodiments. On the contrary, the invention encompasses each new feature as well as any combination of features, in particular including any combination of features in the claims, even if this feature or this combination itself is not explicitly given in the claims or in the embodiments.

The applicant reserves the right to claim all the features disclosed in the application documents as essential to the invention in so far as they are individually or in combination novel over the prior art.

LIST OF REFERENCE SIGNS

V vertical direction
H horizontal direction
1 plastic parison
1A contact surfaces
1B external surface of the plastic parison
2 transport device
3 sterilization chamber
4 gripping system
5 displacement means
6 further transport device
8 radiation device
40 gripping arms
41, 42 gripping clamps
41A, 41B clamp joints
410A, 410B clamp openings
51 drive roller
52 friction rail
100 device
410A clamp opening
420A clamp opening

The invention claimed is:

1. A device for sterilizing containers,
   with a sterilization chamber and a transport device disposed at least partially inside the sterilization chamber for moving the containers within the sterilization chamber,
   wherein the transport device has at least one gripping system for engaging round and supporting the containers by means of a gripping clamp,
   wherein the gripping system has a displacement means to allow exposure to an external surface of at least one contact surface of the plastic parisons which was previously shielded by the gripping system from a sterilizing medium and/or sterilizing radiation during sterilization within the sterilization chamber,
   wherein the displacement means is formed with at least one drive roller which is disposed rotatably within the gripping clamp and is in force-fit engagement with the container, and
   wherein by means of a rotation of the drive roller about its axis of rotation, relative to gripping arms of the gripping clamp, in one direction of rotation, a rotation of the container around its axis of rotation, relative to the gripping arms can be effected, and
   wherein the two directions of rotation are in each case opposed.

2. The device (100) as claimed in claim 1, wherein the drive roller (51) is rotatable by means of a pneumatic, mechanical, electrical or hydraulic drive.

3. A device (100) for sterilizing containers (1),
   with a sterilization chamber (3) and a transport device (2) disposed at least partially inside the sterilization chamber (3) for moving the containers (1) within the sterilization chamber (3),
   wherein the transport device (2) has at least one gripping system (4) for engaging round and supporting the container (1) by means of a gripping clamp (41),
   wherein the gripping system (4) has a displacement means (5) for displacement during sterilization within the sterilization chamber of contact surfaces (1A) on an external surface (1B) of the container (1) which are shielded by the gripping system (4) from a sterilizing medium and/or sterilizing radiation,
   wherein the displacement means (5) is formed with at least one friction (52) rail, wherein the container (1) is guidable along this friction rail (52) within the sterilization chamber (3), wherein by means of a force-fit engagement between the container (1) and the friction rail (52) the container (1) is rotatable about its axis of rotation within the gripping clamp.

4. The device (100) as claimed in claim 3, wherein a pair of gripping clamps (41, 42) are disposed on different clamp joints (41A, 42A) which lie opposite one another in the horizontal direction (H), wherein the clamp joint (42A) of the further gripping clamp (42) is fastened on a further transport device (6) which is disposed at least partially within the sterilization chamber (3).

5. A device (100) for sterilizing containers (1),
with a sterilization chamber (3) and a transport device (2) disposed at least partially inside the sterilization chamber (3) for moving the container (1) within the sterilization chamber (3),
wherein the transport device (2) has at least one gripping system (4) for engaging round and supporting the container (1) by means of a gripping clamp (41),
wherein the gripping system (4) has a displacement means (5) for displacement during sterilization within the sterilization chamber of contact surfaces (1A) on an external surface (1B) of the container (1) which are shielded by the gripping system (4) from a sterilizing medium and/or sterilizing radiation,
wherein the displacement means (5) is formed with at least one further gripping clamp (42),
wherein both gripping clamps (41, 42) are disposed so that they overlap at least partially in the vertical direction (V) and are spaced apart from each another in this direction, and during the sterilization at least one gripping clamp is operatable in an open position and a gripping clamp which is different therefrom is operatable in a closed position, and
after a predeterminable partial sterilization time the respective other gripping clamp is operatable in an open position or in a closed position.

6. The device (100) as claimed in claim 5, wherein clamp joints (41A, 42A) of the gripping clamps (41, 42) are disposed above one another in the vertical direction, wherein respective clamp openings (410A, 420A) of the two gripping clamps (41, 42) overlap at least partially in the vertical direction (V).

7. The device (100) as claimed in claim 5, wherein the gripping clamps (41, 42) are disposed on different clamp joints (41A, 42A) which lie opposite one another in the horizontal direction (H), wherein the clamp joint (42A) of the further gripping clamp (42) is fastened on a further transport device (6) which is disposed at least partially within the sterilization chamber (3).

8. A method for sterilizing containers (1), in which
containers (1) are moved by means of a transport device (2) disposed at least partially inside the sterilization chamber (3),
wherein the transport device (2) has at least one gripping system (4) for engaging round and supporting the plastic parisons (1) by means of a gripping clamp (41),
wherein, during a sterilization within the sterilization chamber, after expiry of a predeterminable partial sterilization time at least one contact surface (1A) of the containers (1) which was previously shielded by the gripping system (4) from a sterilizing medium and/or sterilizing radiation is allowed exposure to an external surface (1B) by a displacement means (5).

9. The method as claimed in claim 8, wherein the containers are rotated relative to the gripping system holding the containers with respect to a longitudinal axis of the containers.

\* \* \* \* \*